United States Patent
Nae et al.

(10) Patent No.: US 11,464,468 B2
(45) Date of Patent: Oct. 11, 2022

(54) CT SCAN PARAMETER OPTIMIZATION

(71) Applicant: KONINKLIJKE PHILIPS N.V., Eindhoven (NL)

(72) Inventors: Yael Haya Nae, Haifa (IL); Andrei Feldman, Haifa (IL); Idan Mishlovsky, Kiryat Bailik (IL); Suresh Narayanan, San Marcos, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 112 days.

(21) Appl. No.: 17/251,444

(22) PCT Filed: Jun. 19, 2019

(86) PCT No.: PCT/EP2019/066144
§ 371 (c)(1),
(2) Date: Dec. 11, 2020

(87) PCT Pub. No.: WO2019/243396
PCT Pub. Date: Dec. 26, 2019

(65) Prior Publication Data
US 2021/0251584 A1    Aug. 19, 2021

Related U.S. Application Data

(60) Provisional application No. 62/687,032, filed on Jun. 19, 2018.

(30) Foreign Application Priority Data

Jul. 19, 2018    (EP) ..................... 18184362

(51) Int. Cl.
*A61B 6/03*    (2006.01)
*A61B 6/00*    (2006.01)
(Continued)

(52) U.S. Cl.
CPC .............. *A61B 6/405* (2013.01); *A61B 6/032* (2013.01); *A61B 6/0407* (2013.01); *A61B 6/06* (2013.01); *A61B 6/544* (2013.01)

(58) Field of Classification Search
CPC ....... A61B 6/405; A61B 6/032; A61B 6/0407; A61B 6/06; A61B 6/544; A61B 6/5205;
(Continued)

(56) References Cited

U.S. PATENT DOCUMENTS 6,285,741 B1    9/2001  Ackelsberg
6,870,898 B1    3/2005  von der Haar
(Continued)

FOREIGN PATENT DOCUMENTS

JP    2006212410 A    8/2006

OTHER PUBLICATIONS

PCT International Search Report, International application No. PCT/EP2019/066144, dated Sep. 17, 2019.

*Primary Examiner* — Don K Wong
(74) *Attorney, Agent, or Firm* — Larry Liberchuk

(57) ABSTRACT

The present invention relates to optimizing values for scan parameters for a scan of an object. An object specific exposure time is determined based on a maximal required value of a z-dependent tube current by exposure time product along a z-axis of the object and a maximal available tube current value of a tube used for the scan of the object (140). The maximal available tube current value depends on a tube voltage and maximal electric power of the tube at given focal spot area (110) and the z-dependent tube current by exposure time product profile is based on a dose index value or a pixel noise index value for the scan of the object, the tube voltage, and a z-dependent object size along the (Continued)

z-axis (120). The object specific exposure time is used for determining values of the scan parameters for the scan of the object (150).

13 Claims, 7 Drawing Sheets

(51) Int. Cl.
*A61B 6/04* (2006.01)
*A61B 6/06* (2006.01)

(58) Field of Classification Search
CPC .......... A61B 6/027; A61B 6/542; G06T 2207/10081; G06T 11/005; G06T 11/006; G06T 2207/10116; G06T 7/32; G01N 23/046; G01N 2223/419; H05G 1/34; H05G 1/30; H05G 1/32; H05G 2/00; H05G 1/62; H05G 1/389; H05G 1/38; H05G 1/28; H05G 1/42; H01G 1/46; G05G 1/40

See application file for complete search history.

(56) References Cited

U.S. PATENT DOCUMENTS

| | | |
|---|---|---|
| 2004/0013223 A1 | 1/2004 | Yamazaki |
| 2004/0101105 A1 | 5/2004 | Segawa |
| 2007/0214017 A1* | 9/2007 | Profio .............. A61B 6/467 600/300 |
| 2007/0258559 A1 | 11/2007 | Hur |
| 2009/0016484 A1 | 1/2009 | Wang |
| 2012/0143659 A1 | 6/2012 | Haras |
| 2014/0270053 A1 | 9/2014 | Larson |
| 2016/0183905 A1 | 6/2016 | Lou |

\* cited by examiner

CT SCAN PARAMETER OPTIMIZATION

FIELD OF THE INVENTION

The present invention relates to a computed tomography (CT) device, a CT system, a method for operating the CT device, and a computer program for operating the CT device. In particular the invention relates to a CT device for scan parameter optimization.

BACKGROUND OF THE INVENTION

US 2014/0270053 A1 shows a system for optimizing CT radiation dose in the clinical setting. Mathematical models are used for estimating patient size, image noise, size-specific radiation dose, and image quality targets based on digital image data and radiologists preferences. A prediction model estimates the scanner's tube current modulation and predicts image noise and size-specific radiation dose over a range of patient sizes. An optimization model calculates specific scanner settings needed to attain target image quality at the minimum radiation dose possible. An automated system processes the image and dose data according to the mathematical models and stores and displays the information, enabling verification and ongoing monitoring of consistent dose optimization.

SUMMARY OF THE INVENTION

It can be seen as an object of the present invention to provide a CT device, a CT system, a method for operating the CT device, a computer program, and a computer readable medium which allow optimizing values of scan parameters for a scan of an object.

In a first aspect of the present invention a CT device for optimizing values of scan parameters for a scan of an object is presented. The CT device comprises an exposure time determination unit and a scan parameter determination unit. The exposure time determination unit is configured for determining an object specific exposure time (ET) based on a maximal required value of a z-dependent tube current by exposure time product profile (max(mAs)) along a z-axis of the object and a maximal available tube current (max(mA)) value of a tube used for the scan of the object. The maximal available tube current value depends on a tube voltage and maximal electric power of the tube at given focal spot area. The z-dependent tube current by exposure time product (mAs(z)) profile is based on a dose index value or a pixel noise index value for the scan of the object, the tube voltage, and a z-dependent object size (object size(z)) along the z-axis. The scan parameter determination unit is configured for determining the values of the scan parameters for the scan of the object based on the object specific ET.

Since the exposure time determination unit of the CT device is configured for determining the object specific ET based on the max(mAs) along the z-axis and the max(mA), a reduced ET can be achieved that allows to determine values of the scan parameters that allow to achieve an image quality that allows to derive details of interest of the object from the image of the scan of the object sufficient for analyzing the object, for example for answering a clinical question. The CT device allows to achieve an appropriate pixel noise and to reduce motion artifacts, in particular motion artifacts in chest and abdomen scans of a patient and in CT angiography (CTA). Since the object specific ET is determined for the scan of the object, too long ET is avoided which reduces motion artifacts. Furthermore, since the object specific ET is determined for the scan of the object, too short ET is avoided. Too short ET may lead to clipped mAs(z) profiles which may result in generation of images with bad image quality, i.e., images with poor signal-to-noise ratio.

The scan parameters can include collimation aperture, rotation time (RT), pitch, dose, time dependent tube current (mA(t)) profile of the tube, time dependent electric power (power(t)) profile of the tube, and/or tube voltage of the tube. The tube can be part of the CT device or connected to the CT device. The scan parameters can additionally include noise reduction tools, noise reduction levels, reconstruction kernels, and/or values for slice thickness. One or more of the scan parameters can be constant during the scan of the object, e.g., the collimation aperture, the RT, and/or the pitch. One or more of the scan parameters can be time dependent during the scan of the object, for example the mA(t) profile and/or the power(t) profile. The scan parameters can for example be collimation aperture, RT, and pitch. The scan parameters can also for example be collimation aperture, RT, pitch, and dose. The object can for example be a part of a body of a patient.

ET is the time for which the isocenter of the object is irradiated. The ET can be expressed as $$ET = \frac{RT}{\text{pitch}} = \frac{\text{collimation}}{\text{table speed}},$$

with RT being a rotation time of the tube around the object in seconds, pitch being table feed normalized to a collimation aperture in one rotation, collimation being the collimation aperture at the isocenter level in mm, and table speed being a translational speed of a table on which the object is placed for the scan in mm/s. The table can be part of the CT device or of a CT system to which the CT device is connected. The table speed can be calculated as $$\text{table speed} = \text{collimation} \cdot \frac{\text{pitch}}{RT}.$$

The object specific ET can be determined based on $$ET = \frac{\max(\text{tube current by exposure time product})}{\max(\text{tube current})} = \frac{\max(mAs)}{\max(mA)}.$$

The max(mA) is a function of the tube voltage and the maximal electric power of the tube at the given focal spot area used for the scan of the object. The max(mA) can also be a function of the tube specifications, which include maximal electric power of the tube, the tube voltage, and focal spot area.

The tube current by exposure time product (mAs) can be expressed as $$mAs = mA \cdot \frac{RT}{\text{pitch}} = mA \cdot ET,$$

with mA being the tube current (mA). The mAs along the z-axis of the object is expressed as the mAs(z) profile. The mAs(z) profile and the max(mAs) can be provided to the exposure time determination unit, e.g. via a wireless or wired connection from an external device such as a server or they can be provided as input from a user. The mAs(z) profile can for example be generated based on methods known from the art, e.g. based on automatic current selection (ACS), longitudinal dose modulation and/or angular dose modulation, for example using Dose Right Index (DRI), z-axis dose modulation (Z-DOM), and/or three-dimensional dose modulation (3D-DOM) taking into account object attenuation along the z-axis of the object and the tube voltage. Alternatively or additionally the exposure time determination unit can be configured for determining the mAs(z) profile and the max(mAs) based on the dose index value or the pixel noise index value for the scan of the object, the tube voltage, and the object size(z) along the z-axis of the object. The dose index value or the pixel noise value, the tube voltage, and the object size(z) along the z-axis of the object can be provided to the exposure time determination unit, e.g. via a wireless or wired connection from an external device such as a server or they can be provided as input from a user. The object size(z) corresponds to a z-dependent attenuation profile of the object.

In operation, the CT device uses a time dependent mA (mA(t)) profile and the object specific ET as input for performing the scan of the object according to the mAs(z) profile. There is a large number of combinations of mA(t) profiles and ETs that allow to scan the object according to the same mAs(z) profile, e.g., an mA(t) profile with shorter scan time and consequently shorter ET and higher mA and another mA(t) profile with longer scan time, longer ET, and lower mA can lead to a scan of the object according to the same mAs(z) profile. The scan time is defined as $$\text{scan time} = \frac{\text{scan length}}{\text{table speed}}.$$

The mA(t) profile in combination with the shorter scan time has a shorter ET than the mA(t) profile with the longer scan time. The mA(t) profile used for the scan can be generated based on the mAs(z) profile, the determined values of the scan parameters and the object specific ET.

The CT device can be used in various scenarios for acquiring images of a part of a body of a patient, such as in CTA, lung diseases, abdomen diseases, trauma, stroke, or cardiac emergencies. The acquired images can have motion artifacts stemming from motion of the body of the patient or parts of the body of the patient, such as organs, e.g., lung, heart, and bowel. The CT device allows to achieve an adequate image quality with appropriate pixel noise and reduced motion artifacts as a shorter ET results in less motion artifacts in images generated from the scan of the object. The CT device allows an improved determination of the values of the scan parameters for the scan of the object. The values of the scan parameters determined using the CT device allow to achieve an improved image quality, i.e., images with improved signal-to-noise ratio.

The scan parameter determination unit can be configured for determining the values of the scan parameters based on maximizing a Figure of Merit (FOM) that is defined as $$FOM = \frac{\text{table speed}^a}{\text{exposure time}^b \cdot \text{dose length product}^c},$$

with a, b and c being constant. In case that the object is a body of a patient or a part of the body of the patient, a user of the CT device is interested in finishing the scan as fast as possible in order to allow the patient to hold the breath during the scan. The table speed depends on collimation aperture, pitch, and RT, i.e., $$\text{table speed} = \text{collimation} \cdot \frac{\text{pitch}}{RT}.$$

A higher table speed allows the patient to more easily hold the breath, as the patient needs to hold the breath for a shorter duration and this allows to reduce motion artifacts in images acquired from the scan. While increasing collimation aperture increases the table speed, it also increases the ET, i.e., as $$ET = \frac{\text{collimation}}{\text{table speed}}.$$

Maximizing the FOM allows to find optimized values for the scan parameters, e.g. collimation aperture, pitch, and RT. Using the FOM can allow to find an optimized object specific ET for determining optimized values for the scan parameters for the specific scan of the object. The FOM can be $$FOM = \frac{\text{table speed}}{ET},$$

with a=1, b=1,c=0. A higher FOM value allows to acquire images from the scan of the object with better image quality as motion artifacts can be reduced for higher FOM values. The scan parameter determination unit can be configured to set the constants a, b and c in dependence of the object that is to be scanned. For example, a larger a value than b value can be chosen in CTA carotids studies, as in this case very fast scans are required in order to avoid jugular contamination and the carotid anatomy is less sensitive to motion artifacts. For example, a larger b value than a value can be chosen for a lung scan as motion artifacts stemming from heart motion are present in the images acquired from the scan and the motion artifacts can be reduced for a shorter ET. Low b and c values are for example chosen if the object is an infant and a pediatric scan is performed in order to reduce the dose and ET of the infant.

The CT device can comprise a tube status determination unit. The tube status determination unit can be configured for determining a current tube status. The current tube status can for example include a current temperature of the tube, a current maximal electric power of the tube, or a current maximal tube voltage. The tube status determination unit can furthermore be configured for determining whether the tube can perform the scan of the object based on the determined values of the scan parameters and the current tube status. The tube can be configured to only perform the scan of the object when the tube can perform the scan of the object based on the determined values of the scan parameters. This allows to ensure functionality of the tube, as the scan of the object is only performed when the current tube capabilities allow to perform the scan using the values of the scan parameters. Furthermore this allows to prevent a scan that may potentially damage the tube. The exposure time determination unit can be configured for increasing the object specific ET in case that the tube cannot perform the scan based on the determined values of the scan parameters. The scan parameter determination unit can be configured to clip the mAs(z) profile in case that the tube cannot perform the scan based on the determined values of the scan parameters. This allows to perform the scan of the object even if the tube cannot perform the scan based on the originally determined values of the scan parameters. If the object specific ET is increased, the scan parameter determination unit can determine adapted values of the scan parameters for the scan of the object based on the increased object specific ET. This allows to perform the scan of the object based on adapted values of the scan parameters.

The tube status determination unit can be a heat calculator unit. The heat calculator unit can be configured for determining whether the heat generated during the scan of the object using the determined values of the scan parameters is acceptable for the tube based on the current tube status and the determined values of the scan parameters. The current tube status can include a current temperature of the tube or current temperature of one or more parts of the tube, e.g., a focal spot area, an anode body, and/or a tube housing. This allows to prevent performing a scan that may potentially damage the tube or one or more parts of the tube. Additionally, no assumptions regarding the tube temperature are required for determining whether the scan of the object can be performed with the tube. Values of the scan parameters for the scan of the object can be determined without a risk of overestimating or underestimating the values of the scan parameters. This allows to determine an optimized mA(t) profile and to provide optimized values of the scan parameters.

The tube status determination unit can be configured for determining a duration until the scan can be performed based on the determined values of the scan parameters. For example if the tube status determination unit is a heat calculator unit, the heat calculator unit can be configured to determine a duration for the tube to cool down to a temperature at which the scan of the object can be performed based on the determined values of the scan parameters. This allows the user to perform the scan of the object based on the determined values of the scan parameters after a predetermined waiting time. The user can be informed about the waiting time in order to better plan the scan of the object.

The scan parameter determination unit can be configured for iteratively adapting one or more values of the scan parameters until an end condition occurs. One end condition can for example be that the tube can perform the scan of the object based on the adapted values of the scan parameters. Another end condition can be that a difference of the values of the scan parameters between two subsequent iteration steps is below a threshold value. Yet another end condition can be that a user manually selects to perform the scan based on the values of the scan parameters determined in the current iteration step. Adapting the values of the scan parameters iteratively allows to find improved values of the scan parameters.

The scan parameter determination unit can be configured for adapting the object specific ET in each iteration step, e.g., by increasing the object specific ET. The scan parameter determination unit can be configured for determining adapted values of the scan parameters for the scan of the object based on the adapted object specific ET in each iteration step and the tube status determination unit can be configured for determining a current tube status in each iteration step and whether the tube can perform the scan of the object based on the adapted values of the scan parameters and the current tube status in each iteration step. Adapting the object specific ET leads to adapted values of the scan parameters, as the values of the scan parameters are determined based on the object specific ET.

The scan parameters can include collimation aperture, RT, and pitch. The scan parameters can also include collimation aperture, RT, pitch, table speed, and/or tube voltage. The adapted one or more values of the scan parameters can for example be values of the collimation aperture, the RT, the pitch, the table speed, and/or the tube voltage. As the object specific ET depends on the collimation aperture, the RT, the pitch and the table speed, the object specific ET can be adapted by adapting the values of the scan parameters as well. Adapting the values of the scan parameters and object specific ET iteratively allows to find improved values of the scan parameters and leads to a better image quality. Furthermore, instead of using the determined values of the scan parameters that have the maximal FOM value for the scan but which are not acceptable for the tube based on the current tube status, adapted values of the scan parameters can be used that allow the tube to perform the scan of the object. This allows to perform the scan of the object with adapted values of the scan parameters optimized to the FOM in dependence of current tube status.

The scan parameter determination unit can be configured for selecting a peak kilovoltage (kVp) as tube voltage that minimizes the object specific ET and maximizes the FOM. The tube voltage can for example be a constant voltage signal. The kVp can for example be a value between 80 to 140 kV, such as 80, 100, 120 or 140 kV. The scan parameter determination unit can be configured to adapt the tube voltage when the maximum mA that the tube can support is reached for a current kVp, e.g. for an initial kVp or a kVp of a current iteration step. Increasing the tube voltage allows to achieve a shorter object specific ET. The scan parameter determination unit can be configured to adapt the tube voltage such that the CT dose index (CTDI) value is kept constant. The CTDI is a function of the tube voltage, mAs, and collimation aperture. The scan parameter determination unit can be configured to keep the CTDI constant by adapting the mAs such that the mAs is lowered when the tube voltage is increased and such that the mAs is increased when the tube voltage is lowered. This allows to keep the pixel noise almost constant. The CTDI value at a constant mAs can be approximated as a function of the kVp as $CTDI \sim kVp^d$, with constant d depending on tube specifications, for example $CTDI \sim kVp^{2.9}$. The mAs ratio for changing kVp is inversely proportional to $kVp^{2.9}$ as the dose is proportional to mAs, i.e., $$\left(\frac{mAs_1}{mAs_2}\right) = \left(\frac{kVp_2}{kVp_1}\right)^{2.9}.$$

Using that mAs=mA·ET yields $$\left(\frac{mA_1 \cdot ET_1}{mA_2 \cdot ET_2}\right) = \left(\frac{kVp_2}{kVp_1}\right)^{2.9}.$$

Electric power is defined as P=U·I=kVp·mA. If the maximal electrical power of the tube is kVp invariant, it follows that $$\max(P_1) = kVp_1 \cdot \max(mA_1) =$$

$$kVp_2 \cdot \max(mA_2) = \max(P_2) \text{ and } \frac{\max(mA_1)}{\max(mA_2)} = \frac{kVp_2}{kVp_1}.$$

This can be inserted in $$\left(\frac{mA_1 \cdot ET_1}{mA_2 \cdot ET_2}\right) = \left(\frac{kVp_2}{kVp_1}\right)^{2.9}$$

for the case of maximal mA, yielding $$\left(\frac{ET_1}{ET_2}\right) = \left(\frac{kVp_2}{kVp_1}\right)^{1.9}.$$

Increasing the tube voltage from $kVp_1$ to $kVp_2$ while keeping the CTDI value constant allows to reduce the object specific ET by up to $$\left(\frac{kVp_2}{kVp_1}\right)^{1.9}.$$

The scan parameter determination unit can be configured for determining the values of the scan parameters based on a look up table that comprises values of the scan parameters in dependence of ET. The look up table can for example include values of scan parameters, such as collimation aperture, RT, and pitch associated to a specific ET. The values of the scan parameters can be provided in the look up table such that the values of the scan parameters maximize the FOM while considering only values that are available from a CT system used for performing the scan of the object. This allows to determine values of the scan parameters that can be used by the CT system for the scan of the object and which are object specific and specific for the CT system used for performing the scan. For example, if the look up table is provided for a CT system providing collimation apertures at the isocenter level of 40 mm, 60 mm, and 80 mm, the values of the scan parameters are optimized such that the collimation apertures can only be 40 mm, 60 mm, or 80 mm. The scan parameter determination unit can also be configured for determining the values of the scan parameters based on scan parameter functions that provide values for the scan parameters in dependence of ET. The look up table and the scan parameter functions allow an easy determination of the values of the scan parameters in dependence of the object specific ET.

The CT device can comprise an object size determination unit. The object size determination unit can be configured for determining an object size(z) of the object along the z-axis. The object size determination unit can be configured for determining the object size(z) of the object along the z-axis based on a two-dimensional X-ray projection image of the object. The two-dimensional X-ray projection image of the object can be acquired by the CT device or can be provided to the CT device.

The CT device can comprise a tube power profile generation unit. The tube power profile generation unit is configured for generating a power(t) profile. The tube power profile generation unit can be configured for generating a mA(t) profile based on the object specific ET, the determined values of the scan parameters, and the mAs(z) profile. Additionally, the tube power profile generation unit can be configured for determining the power(t) profile based on the mA(t) profile and the tube voltage used for the scan of the object.

The tube status determination unit can be configured for determining whether the tube can perform the scan of the object based on the power(t) profile and the current tube status. The power(t) profile and the determined values of the scan parameters can be used for performing the scan of the object.

The heat calculator unit can be configured to determine whether a temperature threshold value is exceeded when performing the scan of the object based on the power(t) profile. The temperature threshold value can be associated with a temperature value for which at least one part of the tube is damaged when the scan of the object is performed based on the determined values of the scan parameters.

The heat calculator unit can be configured to determine the duration for the tube to cool down to a temperature at which the scan can be performed for a certain power(t) profile by iteratively adding time delays at the beginning of the power(t) profile with zero power until the scan of the object can be performed. The duration until the tube can perform the scan using the determined values of the scan parameters corresponds to the added time delays.

In a further aspect of the present invention a spiral CT system is presented. The spiral CT system comprises a CT device according to one of the claims 1 to 9 or any embodiment of the CT device, a tube for emitting X-rays, a table configured for translating an object along a z-axis through the spiral CT system, and a detector for receiving the X-rays. The table is arranged between the tube and the detector such that X-rays emitted from the tube penetrate the object on the table and such that the X-rays are received by the detector. The spiral CT system can comprise a rotatable gantry including the tube and detector which is configured for rotating the tube and the detector in a spiral motion around the object on the table when the table is translated along the z-axis in order to perform spiral CT scanning. The spiral CT system is configured for generating CT images by performing a scan of the object. The CT system allows to achieve improved image quality with less motion artifacts and adequate pixel noise.

In an alternative embodiment the CT device can be connected to a spiral CT system comprising a tube for emitting X-rays, a table configured for translating an object along a z-axis through the spiral CT system, and a detector for receiving the X-rays, i.e., in the alternative embodiment the CT device is not part of the spiral CT system.

In a further aspect of the present invention a method for operating the CT device according to one of the claims 1 to 9 or any embodiment of the CT device is presented. In the method an object specific ET is determined based on a max(mAs) value along a z-axis of an object and a max(mA) value of a tube used for a scan of the object. The max(mA) value depends on a tube voltage and maximal electric power of the tube at given focal spot area. The mAs(z) profile is based on a dose index value or a pixel noise index value for the scan of the object, the tube voltage, and an object size(z) along the z-axis. Values of scan parameters for the scan of the object are determined based on the object specific ET.

The method allows an improved determination of the values of the scan parameters for the scan of the object. The values of the scan parameters determined using the method allow to achieve an improved image quality.

The method can comprise one or more of the following steps:
- providing the object size(z) along a z-axis of the object to be scanned, the dose index value or the pixel noise index value for the scan of the object, the maximal electric power of the tube at given focal spot area, and the tube voltage applied to the tube for the scan of the object,
- calculating the max(mA) value of the tube based on the tube voltage and the maximal electric power of the tube at the given focal spot area,
- calculating the mAs(z) profile along the z-axis based on the dose index value or the pixel noise index value, the tube voltage and the object size(z) along the z-axis,
- extracting the max(mAs) along the z-axis,
- calculating the object specific ET based on the max(mAs) value along the z-axis and the max(mA) value,
- determining the values of the scan parameters for the scan of the object based on the object specific ET,
- generating a mA(t) profile based on the object specific ET, the mAs(z) profile along the z-axis, and the determined values of the scan parameters, and/or
- generating a power(t) profile based on the mA(t) profile and the tube voltage applied to the tube for the scan of the object.

The tube and an according CT system in which the tube is integrated can be operated based on the power(t) profile and the determined values of the scan parameters.

The object size(z) along the z-axis can be calculated based on an image of the object. The object size(z) along the z-axis can also be determined based on a two-dimensional projection image of the object, e.g., a two-dimensional X-ray projection image of the object. The object size(z) along the z-axis can for example be calculated based on a CT image of the object. The object can for example be a part of a body of a patient.

The tube voltage can be provided by the user as kVp value. The tube voltage can be optimized for the scan of the object, e.g., providing a kVp value that maximizes the FOM and/or minimizes the object specific ET.

The max(mA) value for calculating the object specific ET can be a function of tube type, including maximal electric power of the tube used for the scan of the object, focal spot area, and tube voltage.

The values for the scan parameters can be determined by looking up the values of the scan parameters in a look up table which comprises values of ET and values of the scan parameters, such that a value for each of the scan parameters is associated to a specific ET. The object specific ET can be used as input in order to determine the values of the scan parameters. Alternatively scan parameter functions can be provided that depend on ET and provide a value for one or more of the scan parameters in dependence of ET.

The scan parameters can include collimation aperture, RT, pitch, dose, and/or tube voltage. The scan parameters can for example be collimation, RT, and pitch. The scan parameters can also be collimation, RT, pitch, and dose.

The method can furthermore comprise a step:
- determining a current tube status of the tube.

The current tube status can for example include a current temperature of the tube, a current maximal electric power of the tube, or a current maximal tube voltage. The current tube status can also for example include a current temperature of one or more parts of the tube, e.g., a focal spot area, an anode body, and/or a tube housing.

The method can additionally comprise a step:
- determining whether the tube can perform the scan of the object based on the power(t) profile and the current tube status of the tube.

Determining whether the tube can perform the scan of the object based on the power(t) profile and the current tube status of the tube can be performed by a heat calculator unit. The heat calculator unit can determine the temperature of the tube or parts of the tube as current tube status. The heat calculator unit can use the power(t) profile and the current tube status as input and determine whether the tube can perform the scan of the object based on the power(t) profile. The tube can be operated based on the power(t) profile and the determined values of the scan parameters when operation is approved by the heat calculator unit. The method can comprise a step for determining whether a temperature threshold value is exceeded when performing the scan of the object based on the power(t) profile. The temperature threshold value can be associated with a temperature value for which at least one part of the tube is damaged when the scan is performed based on the determined values of the scan parameters.

The method can comprise the step:
- operating the tube based on the power(t) profile and the determined values of the scan parameters if the tube can perform the scan of the object based on the power(t) profile and the current tube status or
- adapting the values of the scan parameters if the tube cannot perform the scan of the object based on the power(t) profile and the current tube status.

The step of adapting the values of the scan parameters if the tube cannot perform the scan of the object based on the power(t) profile and the current tube status, can comprise a step of increasing the object specific ET or clipping the mAs(z) profile. The values of the scan parameters can be adapted based on the increased object specific ET, e.g., by selecting the values of the scan parameters in the look up table associated with the increased object specific ET. Whether the object specific ET is increased or whether the mAs(z) profile is clipped if the tube cannot perform the scan of the object based on the power(t) profile and the current tube status, can be determined based on a task for which the scan of the object is performed, e.g. a clinical question that shall be answered by performing the scan of the object.

The method can comprise the step:
- determining a duration for the tube to cool down to a temperature at which the scan of the object can be performed based on a certain power(t) profile with the determined values of the scan parameters.

The duration for the tube to cool down can be determined by iteratively adding time delays at the beginning of the power(t) profile with zero power until the scan can be performed based on the as adapted power(t) profile and the current tube status. The duration until the tube can perform the scan using the certain power(t) profile corresponds to the added time delays.

The values of the scan parameters can be used for operating the tube, CT device, or CT system, or they can be further optimized in dependence of the current tube status of the tube.

The method can comprise a step of iteratively adapting the values of the scan parameters until an end condition occurs. One end condition can for example be that the tube can perform the scan of the object based on the adapted values of the scan parameters. Another end condition can be that a difference of the values of the scan parameters between two subsequent iteration steps is below a threshold value. Yet another end condition can be that a user manually selects to perform the scan based on the values of the scan parameters determined in the current iteration step. Adapting the values of the scan parameters iteratively allows to find improved values of the scan parameters.

In a further aspect of the present invention a computer program for operating the CT device according to one of the claims 1 to 9 or any embodiment of the CT device is presented. The computer program comprises program code means for causing a processor to carry out the method as defined in claim 11 or any embodiment of the method, when the computer program is run on the processor.

In a further aspect a computer readable medium having stored the computer program of claim 14 is presented. Alternatively or additionally the computer readable medium can have the computer program according to any embodiment of the computer program stored.

It shall be understood that the CT device of claim 1, the method of claim 11, the computer program of claim 14, and the computer readable medium of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
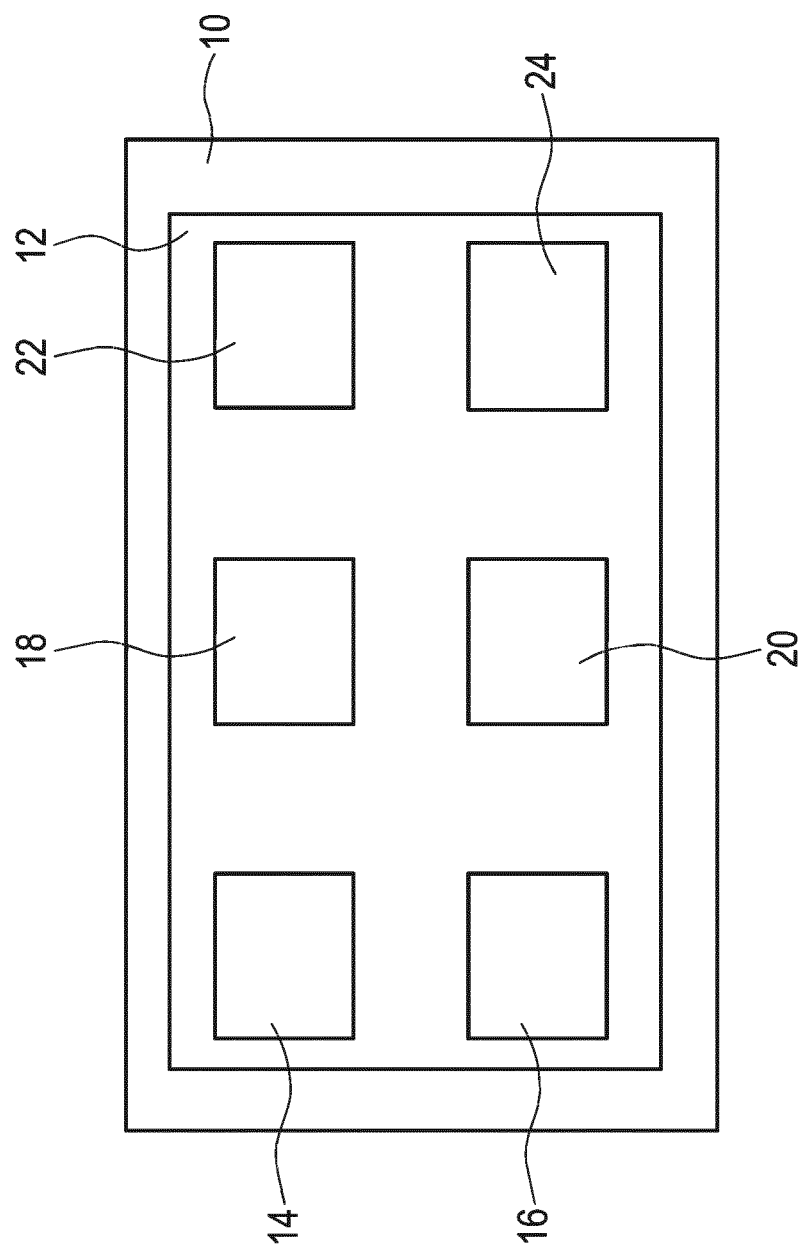
FIG. 1 shows schematically and exemplarily an embodiment of a CT device.

FIG. 1 shows schematically and exemplarily an embodiment of a CT device 10. The CT device 10 can be used for optimizing values of scan parameters for a scan of an object. The object can be a part of a body of a patient. The CT device 10 can for example be used in CTA for acquiring images of the body of the patient or images of parts of the body of the patient.

The CT device 10 comprises a processor 12, which in this embodiment includes an object size determination unit 14, an exposure time determination unit 16, a scan parameter determination unit 18, a tube power profile generation unit 20, a tube status determination unit in form of a heat calculator unit 22, and a computer readable medium in form of memory 24. In other embodiments the exposure time determination unit, the scan parameter determination unit, the tube status determination unit, the object size determination unit, and the tube power profile generation unit can be implemented as integrated circuits. Yet in other embodiments the CT device includes only the exposure time determination unit and the scan parameter determination unit. The tube status determination unit, the object size determination unit, the tube power profile generation unit, and the computer readable medium are optional.

The object size determination unit 14 determines an object size(z) along the z-axis based on a two-dimensional X-ray projection image of the object. The object size(z) corresponds to an attenuation profile along the z-axis of the object. The two-dimensional X-ray projection image of the object in this embodiment is provided by a CT system, in which the CT device 10 can be integrated (cf. FIG. 5). In other embodiments, an image can be acquired by the CT device or can be provided to the CT device from a server (not shown).

The exposure time determination unit 16 is used to determine an object specific ET. In order to determine the object specific ET in this embodiment, the exposure time determination unit 16 first determines an mAs(z) profile and a max(mAs) value along a z-axis of the object based on a dose index value or a pixel noise index value of the scan of the object, a tube voltage applied to a tube used for the scan of the object and the object size(z) along the z-axis. In this embodiment the dose index value or the pixel noise index value and the tube voltage are provided by the user via a user interface (not shown). The object size(z) along the z-axis is provided from the object size determination unit 14 to the exposure time determination unit 16. In other embodiments the dose index value, the pixel noise index value, the tube voltage and the object size(z) along the z-axis can be provided by the user or can be automatically received.

The exposure time determination unit 16 then determines a max(mA) value based on the specifications of the tube and the tube voltage. The specifications of the tube are determined by the tube type, which includes focal spot area, maximal tube voltage, and maximal electric power at the given focal spot area. The exposure time determination unit 16 finally determines the object specific ET based on the max(mAs) value along the z-axis of the object and the max(mA) value, i.e. in this embodiment object specific $$ET = \frac{\max(mAs)}{\max(mA)}.$$

This allows to minimize motion artifacts, as motion artifacts are minimized for an as short as possible object specific ET, i.e., when mA is maximized. The object specific ET depends on RT and pitch used for the scan of the object and can also be defined based on collimation aperture and table speed, i.e.

$$ET = \frac{RT}{\text{pitch}} = \frac{\text{collimation}}{\text{table speed}}.$$

The table speed can be defined as $$\text{table speed} = \text{collimation} \cdot \frac{\text{pitch}}{RT}.$$

The scan parameter determination unit 18 determines the values of the scan parameters. Values of the scan parameters can include table speed, collimation aperture, RT, pitch, dose, mA(t) profile, power(t) profile, and/or tube voltage. The scan parameters can additionally include noise reduction tools, noise reduction levels, reconstruction kernels, and/or values for slice thickness. Adapted values of slice thickness can for example be used to compensate for pixel noise increase in case of a clipped mAs(z) profile, i.e., if the tube used for performing the scan does not support the mAs(z) profile. In this embodiment collimation aperture, RT, and pitch are determined based on the object specific ET by the scan parameter determination unit 18. Other values of the scan parameters, in particular a mA(t) profile and a power(t) profile are generated by the tube power profile generation unit 22.

In order to determine the values of collimation aperture, RT and pitch, the scan parameter determination unit 18 maximizes a FOM. In this embodiment the FOM is defined as $$FOM = \frac{\text{table speed}}{ET}.$$

In other embodiments the FOM can be $$FOM = \frac{\text{table speed}^a}{\text{exposure time}^b \cdot \text{dose length product}^c},$$

with a, b and c being constant, i.e., in the embodiment of FIG. 1, a and b are equal to 1 and c is equal to 0. The values of a, b, and c depend on the object that is to be scanned and the clinical question associated with the scan. For example, a larger a value than b value can be chosen in CTA carotids studies, as in this case very fast scans are required in order to avoid jugular contamination and the carotid anatomy is less sensitive to motion artifacts. For example, a larger b value than a value can be chosen for a lung scan as motion artifacts stemming from heart motion are present in the images acquired from the scan and the motion artifacts can be reduced for a shorter ET. Low b and c values are for example chosen if the object is an infant and a pediatric scan is performed in order to reduce the dose and ET of the infant.

In this embodiment the scan parameter determination unit 18 uses the object specific ET as input and determines the values of the scan parameters based on a look up table that comprises values of the scan parameters in dependence of ET. In this embodiment the look up table has the following form:

| ET | Collimation | RT | pitch | FOM |
|---|---|---|---|---|
| $ET_1$ | $Coll_1$ | $RT_1$ | $Pitch_1$ | $FOM_1$ |
| $ET_2$ | $Coll_1$ | $RT_1$ | $Pitch_2$ | $FOM_2$ |
| ... | ... | ... | ... | ... |
| $ET_{n-3}$ | $Coll_{n-3}$ | $RT_1$ | $Pitch_{n-3}$ | $FOM_{n-3}$ |
| $ET_{n-2}$ | $Coll_n$ | $RT_{n-2}$ | $Pitch_{n-2}$ | $FOM_{n-2}$ |
| $ET_{n-1}$ | $Coll_n$ | $RT_{n-1}$ | $Pitch_{n-1}$ | $FOM_{n-1}$ |
| $ET_n$ | $Coll_n$ | $RT_n$ | $Pitch_n$ | $FOM_n$ |

While ET, pitch, and FOM values are different in each line, two out of the three scan parameter values, for example collimation aperture and RT, can be equal for two or more lines. The look up table is sorted according to the maximized FOM, i.e. $FOM_1$ has the highest value and the following FOM values $FOM_2, \ldots, FOM_{n-3}, FOM_{n-2}, FOM_{n-1}, FOM_n$ each have a lower value than the preceding FOM. Each of the FOM values is associated to a set of parameter values including values for ET, collimation aperture, RT, and pitch. The FOM values can be different for other tasks, e.g., in case of other clinical questions the parameter value sets lead to different FOM values, as a different equation for calculating the FOM is used. The FOM depends on the constants a, b and c, such that depending on the clinical question the look up table can for example be sorted for providing values of scan parameters for a reduced pixel noise or for a reduced dose. In other embodiments the look up table has other and/or more or less entries, e.g., more lines for more ETs. The look up table can also for example have only columns with ET, collimation, RT, and pitch. In this case other parameters, such as table speed and FOM are calculated based on the values of the parameters included in the look up table.

In yet other embodiments the scan parameter determination unit uses the object specific ET as input to scan parameter functions that provide values for the scan parameters in dependence of ET.

The values of the parameters in the look up table and the values of the parameters that can be determined based on the scan parameter functions are specific to the object to be scanned and a spiral CT system used for performing the scan of the object, i.e., the look up table and the scan parameter functions include the limitations of the spiral CT system. The limitations of the spiral CT systems include limitations to table speed, collimation aperture, RT, pitch, and max (mA). Hence, if for example the spiral CT system offers only a limited number of values for the collimation apertures, the look up table will also only include these values for the collimation apertures. This allows to determine values of the scan parameters that can be used for the scan of the object and which are object specific as well as specific to the spiral CT system used to perform the scan.

The tube power profile generation unit 20 is used to generate the power(t) profile. In a first step the tube power profile generation unit 20 generates the mA(t) profile based on the object specific ET, the mAs(z) profile, and the determined values of the scan parameters. In a second step the tube power profile generation unit 20 determines the power(t) profile based on the mA(t) profile and the tube voltage used for the scan of the object. The power(t) profile and the determined values of the scan parameters can be used for performing the scan of the object.

In this embodiment, before a scan of the object is performed, it is determined whether the tube can perform the scan of the object, i.e., it is determined whether the tube currently supports the scan. This is performed by the heat calculator unit 22.

The heat calculator unit 22 determines a current tube status. The current tube status in this embodiment is a current temperature of a focal spot area of the tube. In other embodiments the current tube status can include a current temperature of the tube or current temperature of one or more parts of the tube, e.g., a focal spot area, an anode body, and/or a tube housing.

The heat calculator unit 22 determines whether the tube can perform the scan of the object based on the determined values of the scan parameters and the current tube status, i.e. the current temperature of the focal spot area. This is done by determining whether the heat generated during the scan of the object using the determined values of the scan parameters is acceptable for the tube based on the current tube status and the determined values of the scan parameters. In particular, the heat calculator unit 22 determines whether the tube can perform the scan of the object based on the current tube status and the power(t) profile generated by the tube power profile generation unit 20. The heat calculator unit 22 therefore determines whether a temperature threshold value is exceeded when performing the scan of the object based on the power(t) profile. The temperature threshold value can be associated with a temperature value for which the focal spot area is damaged when the scan of the object is performed based on the power(t) profile. The temperature threshold value can also be associated with a temperature for which any other part of the tube is damaged when the scan of the object is performed based on the power(t) profile.

The heat calculator unit 22 in this embodiment causes the tube to only perform the scan of the object when the tube can perform the scan of the object based on the determined values of the scan parameters, i.e., the heat calculator unit 22 either approves the scan if the tube supports the scan or it disapproves the scan if the tube does not support the scan. This allows to ensure functionality of the tube, as the scan of the object is only performed when the current tube capabilities allow to perform the scan using the determined values of the scan parameters. Furthermore this allows to prevent a scan that may potentially damage the tube and in particular the focal spot area. In other embodiments the heat calculator unit 22 may only provide a warning to a user regarding the exceeding of the temperature threshold value for the scan of the object using the determined values of the scan parameters.

If the heat calculator unit 22 determined that the tube cannot perform the scan of the object based on the determined values of the scan parameters and the current tube status, the scan parameter determination unit 18 can iteratively adapt one or more values of the scan parameters until an end condition occurs. In this embodiment the end condition is that the tube can perform the scan of the object based on the adapted values of the scan parameters. In other embodiments the end condition can for example be that the difference of the values of the scan parameters between two subsequent iteration steps is below a threshold value. The threshold value can for example be set by the user. The user can also set a threshold value as percentage and/or for each scan parameter individually. Another end condition can for example be that a maximal number of iteration is reached or a predetermined duration, e.g., a cool down duration of the tube, has passed.

In this embodiment the scan parameter determination unit 18 adapts the object specific ET, clips the mA(t) profile (cf. FIG. 4B), or waits until the scan can be performed with the currently determined values of the scan parameters. Whether the scan parameter determination unit 18 adapts the object specific ET, clips the mA(t) profile, or waits, depends on the object to be scanned and which information the user desires to obtain, i.e., it in particular depends on a clinical question.

In this embodiment the scan parameter determination unit 18 includes an iteration counter that counts the number of iterations in which the object specific ET has been adapted. The scan parameter determination unit 18 only adapts the object specific ET if the iteration counter is below a predetermined number, e.g., below 6. The scan parameter determination unit 18 in this embodiment furthermore does not clip the mA(t) profile if the max(mA) value of the clipped mA(t) profile is below a predetermined threshold percentage, e.g. 30%, of the max(mA) value of the original mA(t) profile, i.e., the mA(t) profile originally determined by the tube power profile generation unit 20. The predetermined number and the predetermined threshold percentage depend on the object to be scanned and on the clinical question that is meant to be answered by the scan.

The scan parameter determination unit 18 adapts the object specific ET by increasing the object specific ET, i.e. prolonging the object specific ET. In this embodiment the values of the scan parameters of the next line of the look up table are used as adapted values. For example, instead of using the determined values of the scan parameters associated to $ET_1$, the values of the scan parameters associated to $ET_2$ are used in a first iteration step. This means that the scan parameter determination unit 18 determines the values $Coll_1$, $RT_1$, and $Pitch_2$ as adapted values of the scan parameters for the current first iteration step instead of the originally determined values $Coll_1$, $RT_1$, and $Pitch_1$. Hence also $ET_2$ is used as object specific ET instead of $ET_1$. These values of the scan parameters and the increased object specific ET are then used by the tube power profile generation unit 20 to generate an adapted power(t) profile. The heat calculator unit 22 determines the current tube status. The current tube status, i.e., temperature of the tube, changes between two iteration steps as some time has passed since the tube status was determined. The heat calculator unit 22 then determines whether the scan of the object can be performed based on the current tube status and the power(t) profile. This allows to perform the scan of the object even if the tube cannot perform the scan based on the originally determined values of the scan parameters, since the power(t) profile can be iteratively adapted until the scan of the object can be performed. This allows to perform the scan of the object based on adapted values of the scan parameters.

The scan parameter determination unit 18 clips the mA(t) profile by limiting the max(mA) that is available from the tube. Hence the clipped mA(t) profile has a max(mA) that in combination with the object specific ET would generate a clipped mAs(z) profile. The clipped mA(t) profile is provided to the tube power profile generation unit 20 that generates an adapted power(t) profile. The heat calculator unit 22 determines whether the tube can perform the scan of the object based on the current tube status and the adapted power(t) profile.

If the heat status calculator unit 22 determined that the tube can perform the scan of the object based on the determined values of the scan parameters and the current tube status, the scan of the object can be performed. In this embodiment the display informs the user about the values of scan parameters that can be used for the scan. Furthermore the display informs the user whether the values of the scan parameters that can be used for the scan are the originally determined values of the scan parameters or whether they have been adapted. If the values were adapted the user is provided with the option to wait for the tube to cool down in order to perform the scan with the originally determined values of the scan parameters or to adapt the values of the scan parameters.

In this embodiment the display additionally displays the duration that is required for the tube to cooldown in order to use the originally determined values of the scan parameters. The duration for the tube to cool down is determined by the heat calculator unit 22 by iteratively adding time delays at the beginning of the power(t) profile with zero power until the scan is approved by the heat calculator unit 22. The duration until the tube can perform the scan using the originally determined values of the scan parameters corresponds to the added time delays.

In other embodiments the display can list all sets of determined values of scan parameters that have been determined during the iterative adaption of the values of the scan parameters and the corresponding duration until the respective set of determined values of scan parameters can be used to perform the scan of the object. The heat calculator unit 22 can also be configured to provide a suggestion for waiting for a predetermined duration in order to be able to use one of the sets of determined values of scan parameters that allows to achieve a specific image quality, e.g., sufficient to answer a clinical question. The specific image quality can be predetermined, e.g. depending on the clinical question or can be entered by the user.

The memory 24 stores a computer program that allows to operate the CT device. The computer program comprises program code means for causing the processor 12 to carry out an embodiment of the method as presented in FIGS. 6 and 7, when the computer program is run on the processor 12.

Figure 2:
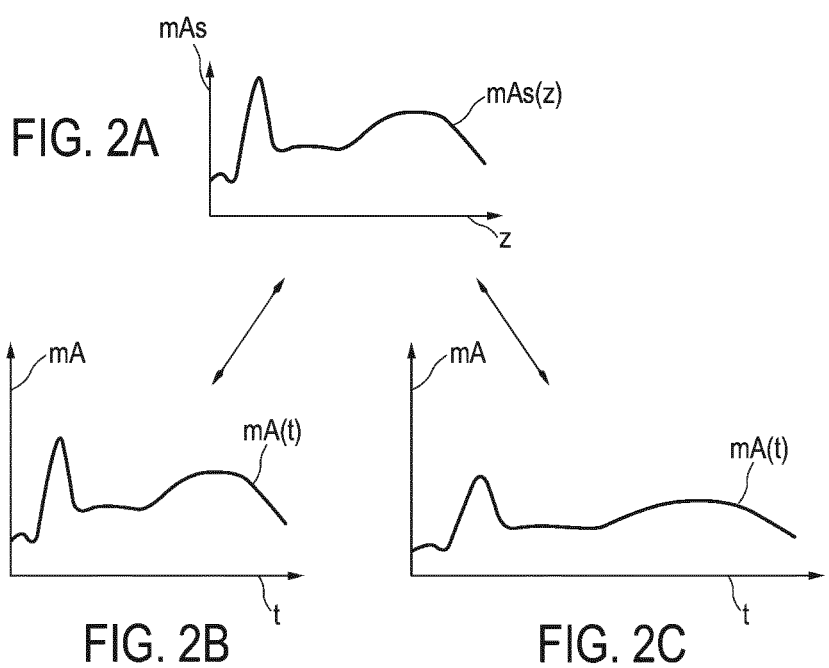
FIG. 2A shows schematically and exemplarily a first mAs(z) profile for a scan of an object.
FIG. 2B shows schematically a first mA(t) profile that can be used to generate the first mAs(z) profile.
FIG. 2C shows schematically a second mA(t) profile that can be used to generate the first mAs(z) profile.

FIG. 2A shows schematically and exemplarily a first mAs(z) profile for a scan of an object. The object in this embodiment is a part of a body of a patient. There is a large number of mA(t) profiles that in combination with a specific ET allow to generate the first mAs(z) profile.

FIG. 2B shows schematically a first mA(t) profile that in combination with a first object specific ET can be used to generate the first mAs(z) profile.

FIG. 2C shows schematically a second mA(t) profile that in combination with a second object specific ET can be used to generate the first mAs(z) profile.

Figure 3:
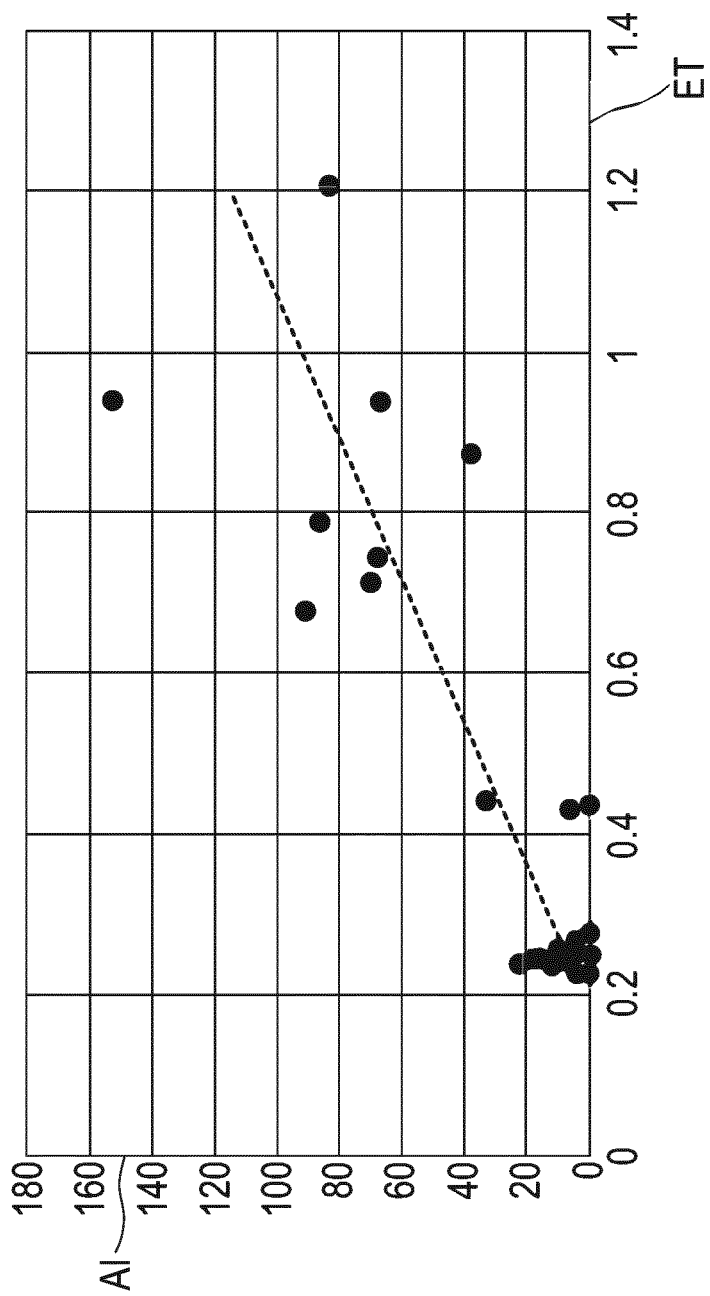
FIG. 3 shows a graph with an artifact index on the vertical axis and ET on the horizontal axis.

FIG. 3 shows a graph with an artifact index AI in mm on the vertical axis and ET in seconds on the horizontal axis. Each of the data points is associated to a clinical data set of chest CT scans of a respective patient. Each data point corresponds to a value of the artifact index AI which is defined as artifact index=amplitude·number of slices with an artifact, i.e. the clinical data represent the artifact indexes defined based on a respective number of images of the respective scan in which a heart double wall artifact appears and the maximal amplitude of the heart double wall artifacts of the images of the chest CT scan of the respective patient. The maximal amplitude of the artifact is a maximal artifact size in mm and all slices have the same slice thickness. The artifact index AI of the respective chest CT scans increases with increasing ET. Reducing ET allows to reduce the artifact index AI.

Figure 4A:
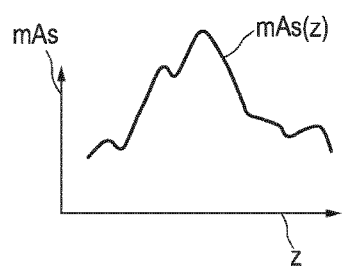
FIG. 4A shows schematically and exemplarily a second mAs(z) profile for a scan of an object.

FIG. 4A shows schematically and exemplarily a second mAs(z) profile for a scan of an object. When a scan of an object requires a max(mAs) value that requires, based on object specific ET, an mA value above the maximal mA value that the tube can be operated with, the mAs value is clipped (cf. FIG. 4C), as follows from $$mA = \frac{mAs}{ET}.$$

Figure 4B:
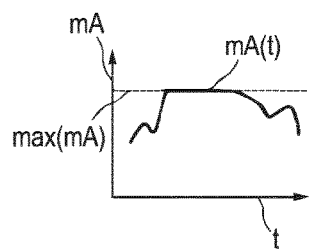
FIG. 4B shows schematically and exemplarily clipping of a mA(t) profile that can be used to generate the second mAs(z) profile.

FIG. 4B shows schematically and exemplarily clipping of a mA(t) profile. For the used ET, the tube used for the scan of the object can only produce a max(mA) below the one required to generate the second mAs(z) profile.

Figure 4C:
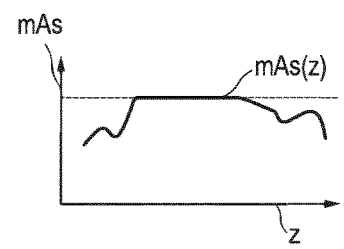
FIG. 4C shows schematically and exemplarily a clipped second mAs(z) profile.

FIG. 4C shows schematically and exemplarily the clipped second mAs(z) profile generated by the combination of the ET and the clipped mA(t) profile of FIG. 4B.

The clipped mAs(z) profile may be useful for generating images with an image quality sufficient for answering specific clinical questions, since short ET is essential for specific clinical needs. In other cases the ET may be prolonged in order to generate images with better image quality that allow to answer different clinical questions.

Figure 5:
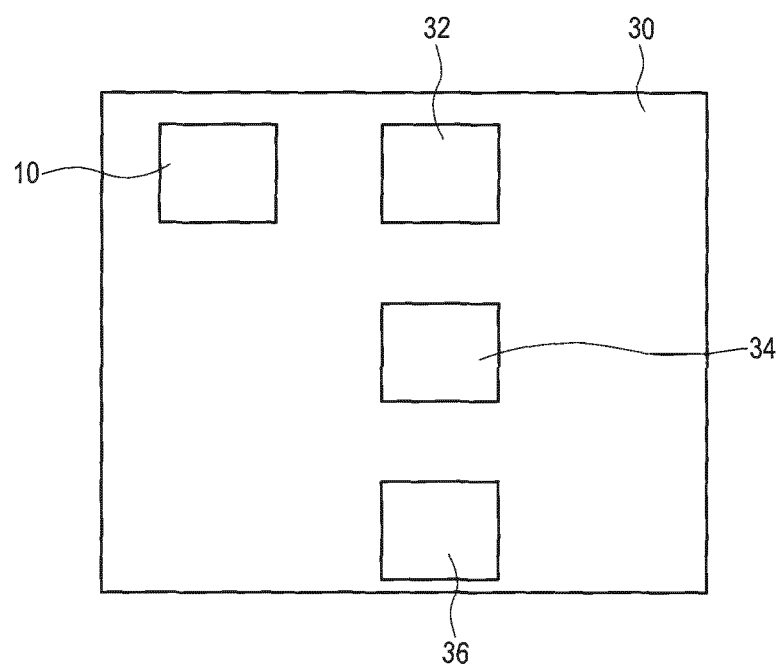
FIG. 5 shows an embodiment of a CT system.

FIG. 5 shows an embodiment of a spiral CT system 30. The spiral CT system 30 includes a CT device 10, a tube 32, a table 34, and a detector 36. The table 34 is arranged between the tube 32 and the detector 36 such that X-rays emitted from the tube 32 can penetrate an object placed on the table 34 and such that the X-rays are received by the detector 36. Various features of the spiral CT system are known to the skilled person and are not shown in detail, e.g., static and rotatable gantries.

The CT device 10 provides values of the scan parameters for a scan of the object that is placed on the table 34. The tube 32 emits X-rays that travel from the tube 32 through the object placed on the table 34 to the detector 36. The table 34 translates along a z-axis through the CT system 30 with a table speed while the tube 32 and the detector 36 rotate in a spiral motion around the object in order to acquire X-ray projection images. The X-ray projection images can be processed in order to generate three-dimensional CT images of the object. The three-dimensional CT images allow to analyze the object. The object can for example be a patient or a part of the body of the patient. The patient or the part of the body of the patient can be scanned in order to answer a clinical question.

Figure 6:
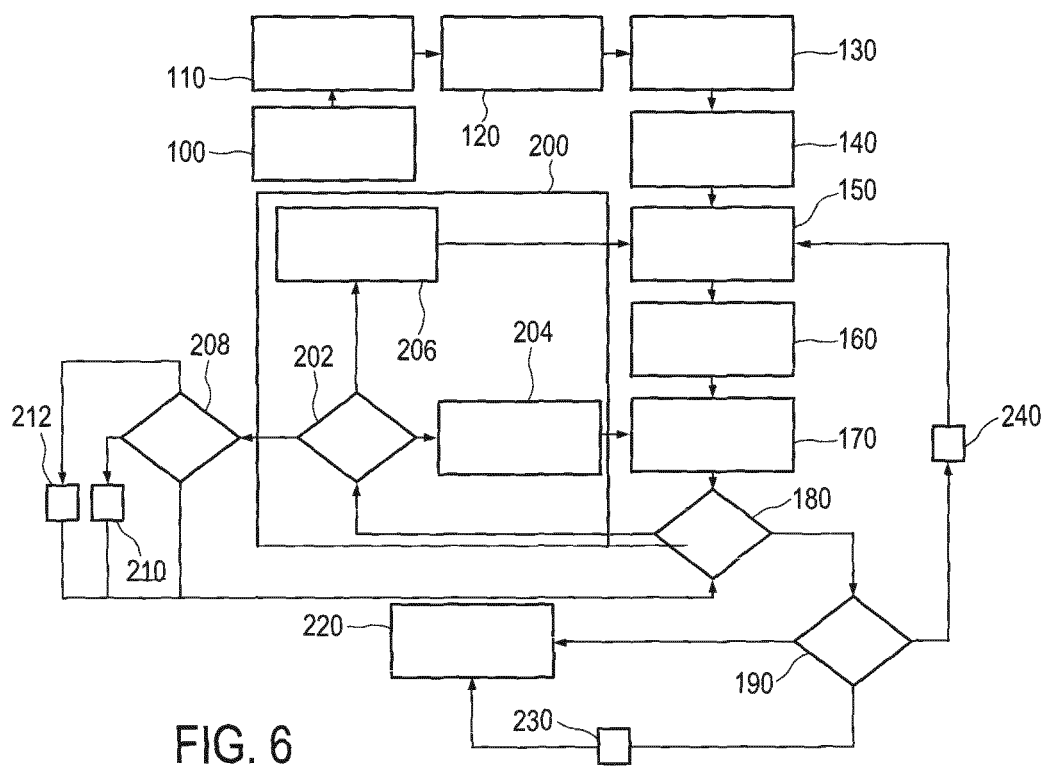
FIG. 6 shows a first embodiment of a method for operating the CT device.

FIG. 6 shows a first embodiment of a method for operating the CT device. The CT device operated using the method can for example be the embodiment of the CT device as presented in FIG. 1. The CT device can be integrated in a spiral CT system, for example the spiral CT system as presented in FIG. 5.

In the method an object specific ET is determined based on a max(mAs) value along a z-axis of an object and a max(mA) value of a tube used for a scan of the object. The max(mA) value depends on a tube voltage and maximal electric power of the tube at given focal spot. The mAs(z) profile is based on a dose index value or a pixel noise index value for the scan of the object, the tube voltage, and an object size(z) along the z-axis. Values of scan parameters for a scan of the object are determined based on the object specific ET. The method allows an improved determination of the values of the scan parameters for the scan of the object. The values of the scan parameters determined using the method allow to achieve an improved image quality. In this embodiment a part of a body of a patient is scanned. In other embodiments other objects can be scanned.

In step 100 the object size(z) in form of a patient size(z) along the z-axis of the part of the body of the patient to be scanned, the dose index value or the pixel noise index value for the scan of the part of the body to be scanned, the maximal electric power of the tube at the given focal spot area, and the tube voltage applied to a tube for the scan of the part of the body to be scanned are provided. The tube voltage is a kVp value selected by the user. In other embodiments an object size(z) of an object can be provided instead of the patient size(z). In this embodiment the patient size(z) along the z-axis is calculated based on a two-dimensional X-ray projection image of the part of the body to be scanned. The two-dimensional X-ray projection image in this embodiment is received from an initial scan of the patient. The patient size(z) along the z-axis corresponds to an attenuation profile along the z-axis. In this embodiment the patient size(z) along the z-axis is represented in terms of water equivalent diameter that represents the size of a circular water phantom that would provide the cross sectional attenuation characteristic of the patient. In other embodiments a two-dimensional X-ray projection image can be provided from a server or the patient size(z) along the z-axis can be calculated or provided in an alternative manner.

In step 110 the max(mA) value of the tube is calculated based on the tube voltage and the maximal electric power of the tube at the given focal spot.

In step 120 the mAs(z) profile along the z-axis is calculated based on the dose index value or the pixel noise index value, the tube voltage, and the patient size(z) along the z-axis.

In step 130 the max(mAs) along the z-axis is extracted.

In step 140 the object specific ET is calculated based on the max(mAs) value along the z-axis and the max(mA) value.

In step 150 the values of the scan parameters for the scan of the part of the body to be scanned are determined based on the object specific ET. In this embodiment the values of the scan parameters are determined by looking up the values of the scan parameters in a look up table which comprises values of ET and values of the scan parameters, such that a value for each of the scan parameters is associated to a specific ET. In other embodiments scan parameter functions can be provided that depend on ET and provide a value for one or more of the scan parameters in dependence of ET. The scan parameters in this embodiment are collimation aperture, RT and pitch. In other embodiments the scan parameters can include collimation aperture, RT, pitch, dose, and/or tube voltage. The look up table is generated based on maximizing a specific FOM. In this embodiment the FOM is defined as $$FOM = \frac{table\ speed}{ET}.$$

In other embodiments the FOM can be $$FOM = \frac{table\ speed^a}{exposure\ time^b \cdot dose\ length\ product^c},$$

with a, b and c being constant. The look up table can be generated in any other manner, e.g., the values can be manually selected by an experienced user.

In step 160 a mA(t) profile is generated based on the object specific ET, the mAs(z) profile along the z-axis, and the determined values of the scan parameters.

In step 170 a power(t) profile is generated based on the mA(t) profile and the tube voltage applied to the tube for the scan of the part of the body.

In step 180 it is determined whether the tube can perform the scan of the part of the body based on the power(t) profile and a current tube status of the tube. In this embodiment the current tube status in form of a current temperature of a focal spot area of the anode of the tube is determined and a heat generated by performing the scan of the part of the body. In other embodiments another tube status can be determined and/or the temperature of other parts of the tube, e.g., the tube housing or the anode. The current tube status and the heat generated by the scan of the part of the body are used to determine whether the tube can perform the scan of the part of the body based on the power(t) profile. In this embodiment it is determined whether the heat generated during the scan of the part of the body using the determined values of the scan parameters is acceptable for the tube based on the current tube status and the determined values of the scan parameters. This is done by determining whether a temperature threshold value is exceeded when performing the scan of the part of the body based on the power(t) profile. The temperature threshold value is associated with a temperature value for which the focal spot area of the anode is damaged when the scan is performed based on the determined values of the scan parameters. In other embodiments the temperature threshold can also be associated with temperature values of other parts of the tube.

If the tube can perform the scan of the part of the body based on the power(t) profile, step 190 is performed, otherwise step 200 is performed.

In step 190 in this embodiment the user is informed about the values of the scan parameters that can be used for the scan. The user is offered the option to perform the scan of the part of the body based on the determined values of the scan parameters in order to perform the scan in step 220. Furthermore the user is informed about other sets of values of the scan parameters that have been determined by the method in case that the values of the scan parameters that can be used for the scan are not the originally determined parameters. If there are adapted values of the scan parameters, the user is provided with the option to wait for the tube to cool down in step 230 in order to perform the scan with the originally determined or specific adapted values of the scan parameters or to adapt the values of the scan parameters in step 240. In this embodiment a duration for a tube to cool down to a level such that a specific set of values of the scan parameters can be used for the scan is determined and displayed to the user for all sets of values of the scan parameters determined by the method. In other embodiments the duration can only be determined when it is requested by the user, e.g., for the originally determined values of the scan parameters. The duration for the tube to cool down is determined by iteratively adding time delays at the beginning of the power(t) profile with zero power until the scan is approved by the process performed in step 180. The duration until the tube can perform the scan using the specific set of values of the scan parameters corresponds to the added time delays.

If the user decides to perform the scan in step 190, the scan of the part of the body is performed based on the determined values of the scan parameters in step 220. In this embodiment, the tube is operated based on the power(t) profile and the determined values of the scan parameters if the tube can perform the scan of the part of the body based on the power(t) profile.

If the user decides to wait for the tube to cool down in step 190, step 230 is performed and the method waits for the tube to cool down. After the tube has cooled down to a temperature that allows to perform the scan based on the originally determined or specific adapted values of the scan parameters, step 220 is performed using the originally determined or the specific adapted values of the scan parameters. In other embodiments step 230 can be followed by step 180 in which it is determined whether the scan can be performed based on the current tube status and the originally determined or the specific adapted values of the scan parameters. If the originally determined values of the scan parameters can be used for the scan, the user is offered to perform the scan based on the originally determined values of the scan parameters in step 190 and the scan can then be performed in step 220 based on the originally determined values of the scan parameters.

If the user decides to adapt the values of the scan parameters in step 190, the user can adapt any of the values of the scan parameters, i.e., in this embodiment collimation aperture, RT, or pitch. In other embodiments other scan parameter values can be available to be adapted. The object specific ET is then calculated for the adapted values of the scan parameters and the previous steps, starting with step 150 are repeated based on the adapted object specific ET. This allows to iteratively adapt the values of the scan parameters.

In other embodiments step 190 can include the limitation that the scan of the part of the body is only allowed if an end condition occurs. The end condition can for example be that a difference of the values of the scan parameters between two subsequent iteration steps is below a threshold value. The threshold value can be set by the user or can be predetermined. In yet other embodiments step 190 can start the scan without feedback from the user or after a predetermined time in which the user can give feedback.

Step 200 adapts the values of the scan parameters if the tube cannot perform the scan of the part of the body based on the power(t) profile. Step 200 includes substeps 202, 204, and 206.

In step 202 it is determined whether the mA(t) profile is clipped in step 204, whether the scan and the object specific ET is prolonged in step 206, or whether a duration for the tube to cool down is calculated in step 208. Whether the object specific ET is increased, whether the mA(t) profile is clipped, or whether the duration for the tube to cool down is calculated, if the tube cannot perform the scan of the part of the body based on the power(t) profile, can be determined based on a clinical question for which the scan of the part of the body is performed. Instead of a clinical question any other task may be considered.

In this embodiment the number of iterations in which the object specific ET is prolonged is counted by an iteration counter. Step 208 is only performed in this embodiment under the conditions that the number of iterations in which the object specific ET was prolonged is above a predetermined threshold value, e.g. above 6, and that the max(mA) value of the clipped mA(t) profile is below a predetermined threshold percentage, e.g. 25%, of the max(mA) value of the original mA(t) profile.

In step 204 the mA(t) profile is clipped by limiting the max(mA) along the time axis. In this embodiment the limiting of the max(mA) along the time axis is limited to a predetermined threshold percentage, e.g. 30%, of the original mA(t) profile. In other embodiments there may be no predetermined threshold percentage or the threshold percentage can be entered by the user. The clipped mA(t) profile is used in step 170 for generating an adapted power(t) profile.

In step 206 the object specific ET is increased. In this embodiment increasing the object specific ET corresponds to moving to the next line of the look up table in step 150 in order to determine adapted values of the scan parameters. The steps following step 150 are repeated. Step 200 can lead to an iterative cycle which ends, when the tube can perform the scan of the part of the body based on an adapted power(t) profile.

In step 208 the duration for the tube to cool down to a temperature at which the scan can be performed based on the current power(t) profile is determined, i.e., it is determined how long it takes before the tube can perform the scan of the part of the body based on the current power(t) profile. In other embodiments step 208 can include a determination of the duration for the tube to cool down to a temperature at which the scan can be performed based on the original power(t) profile or any other adapted power(t) profile. The duration for the tube to cool down is displayed and the user is provided with the options to wait for the tube to cool down in step 210 in order to perform the scan with the respective values of the scan parameters, to adapt the values of the scan parameters in step 212, or to perform step 180. In other embodiments the iteration counter can be reset when step 208 is performed.

Figure 7:
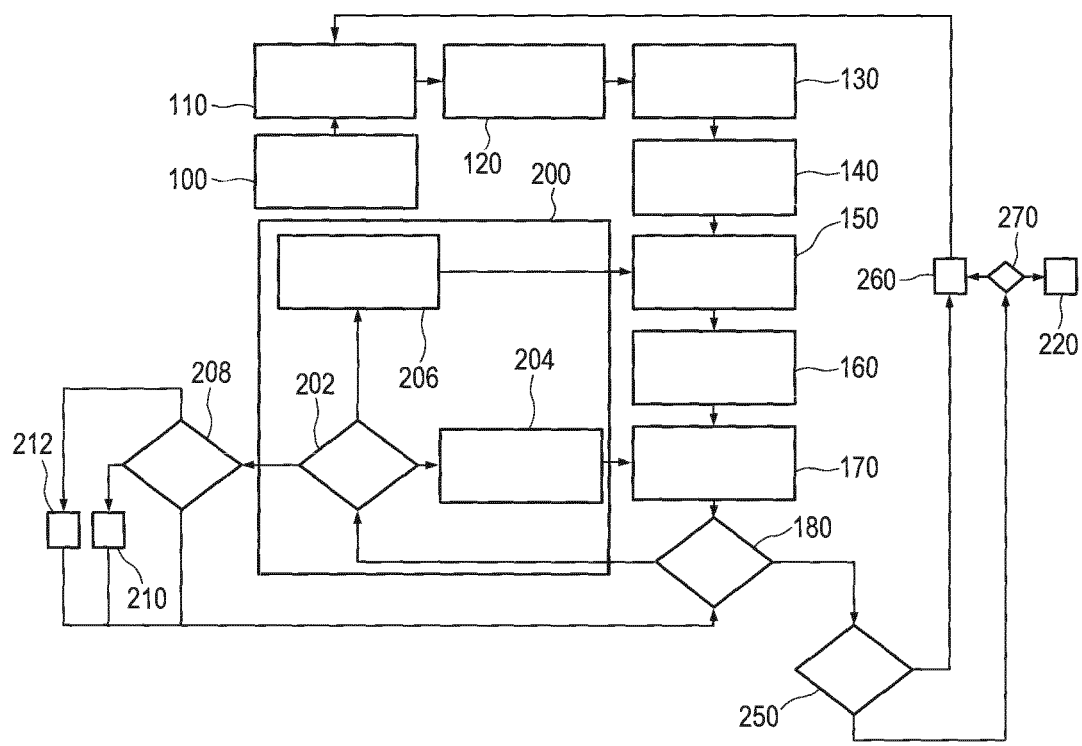
FIG. 7 shows a second embodiment of the method for operating the CT device.

FIG. 7 shows a second embodiment of the method for operating the CT device. In this embodiment of the method the tube voltage can be iteratively adapted in order to optimize the object specific ET.

When at a given tube voltage the max(mA) value that the tube can be operated with is reached, changing the tube voltage can allow to reduce the object specific ET. In order to allow the pixel noise to be kept at least almost constant when changing the tube voltage, the CTDI is kept constant. In this embodiment, this allows to reduce the ET by up to $$\left(\frac{kVp_2}{kVp_1}\right)^{1.9}$$

with $kVp_2$ being the adapted kilovoltage peak of the tube voltage and $kVp_1$ being the previous kilovoltage peak of the tube voltage. Adapting the tube voltage can be used to decrease motion artifacts in scans in which an impact of a high tube voltage on contrast is less relevant and ET can be reduced.

Steps 100 to 180 and 200 to 212 correspond to the steps as presented for the embodiment of the method presented in FIG. 6 with the difference that in step 100 a $kVp_1$ value is provided as kVp value of the tube voltage of the current tube voltage adaption iteration step.

In step 250 it is determined whether one or more iterations according to step 206 have been performed, i.e., whether the object specific ET was changed in order to allow the tube to perform the scan based on adapted values of the scan parameters.

If one or more iterations according to step 206 have been performed the iteration counter is set to zero and the tube voltage is increased to $kVp_2$ in step 260. The determined values of the scan parameters and $kVp_2$ are provided as input to step 110 of the method, i.e., $kVp_2$ becomes the tube voltage of the current tube voltage adaption iteration step meaning $kVp_1$ and the following steps are repeated based on the adapted tube voltage.

If no iterations have been performed, it is determined in step 270 whether max(mA) corresponds to an absolute max(mA), i.e., a maximal tube current that the tube can support at the current $kVp_1$. If the max(mA) is the absolute max(mA), the tube voltage is increased to $kVp_2$ in step 260. The determined values of the scan parameters and $kVp_2$ are provided as input to step 110 of the method and the following steps are repeated. If the mA is not the absolute max (mA), the scan of the part of the body is performed based on the determined values of the scan parameters in step 220. In this embodiment, the tube is operated based on the power(t) profile and the determined values of the scan parameters.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like providing the object size(z) along a z-axis of the object to be scanned, the dose index value or the pixel noise index value for the scan of the object, the maximal electric power of the tube for the given focal spot area, and the tube voltage applied to the tube for the scan of the object, calculating the maximal available tube current value of the tube based on the tube voltage and the maximal electric power of the tube at the given focal spot area, calculating a mAs(z) profile along the z-axis based on the dose index value or the pixel noise index value, the tube voltage, and the object size(z) along the z-axis, extracting the max(mAs) value along the z-axis, calculating the object specific ET based on the max(mAs) value along the z-axis and the max(mA) value, determining the values of the scan parameters for the scan of the object based on the object specific ET, generating a mA(t) profile based on the object specific ET, the mAs(z) profile along the z-axis, and the determined values of the scan parameters, generating a power(t) profile based on the mA(t) profile and the tube voltage applied to the tube for the scan of the object, determining a current tube status of the tube, determining whether the tube can perform the scan of the object based on the power(t) profile and the current tube status, operating the tube based on the power(t) profile and the determined values of the scan parameters if the tube can perform the scan of the object based on the power(t) profile, determining a duration for the tube to cool down to a temperature at which the scan of the object can be performed based on a certain power(t) profile with the determined values of the scan parameters, adapting the values of the scan parameters if the tube cannot perform the scan of the object based on the power(t) profile, et cetera performed by one or several units or devices can be performed by any other number of units or devices. These operations and/or the method can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet, Ethernet, or other wired or wireless telecommunication systems.

Any reference signs in the claims should not be construed as limiting the scope.

The present invention relates to optimizing values for scan parameters for a scan of an object. An object specific exposure time is determined based on a maximal required value of a z-dependent tube current by exposure time product along a z-axis of the object and a maximal available tube current value of a tube used for the scan of the object. The maximal available tube current value depends on a tube voltage and maximal electric power of the tube at given focal spot area and the z-dependent tube current by exposure time product profile is based on a dose index value or a pixel noise index value for the scan of the object, the tube voltage, and a z-dependent object size along the z-axis. The object specific exposure time is used for determining values of the scan parameters for the scan of the object. The values of the scan parameters when used in a scan allow acquiring images with an improved image quality, i.e., with an improved signal-to-noise ratio.

The invention claimed is:

1. A computed tomography device for optimizing values of scan parameters for a scan of an object, the computed tomography device comprising:
   a digital storage memory configured to store processor executable instructions; and
   at least one processor configured to execute the processor executable instructions to:
      determine an object specific exposure time based on a maximal required value of a z-dependent tube current by exposure time product profile along a z-axis of the object and a maximal available tube current value of a tube used for the scan of the object; and
      determine the values of the scan parameters for the scan of the object based on the object specific exposure time, wherein the maximal available tube current value depends on a tube voltage and maximal electric power of the tube at given focal spot area, and wherein the z-dependent tube current by exposure time product profile is based on a dose index value or a pixel noise index value for the scan of the object, the tube voltage, and a z-dependent object size along the z-axis, wherein the scan parameter determination unit is configured for determining the values of the scan parameters based on maximizing a Figure of Merit that is defined as $$\text{Figure of Merit} = \frac{\text{table speed}^a}{\text{exposure time}^b \cdot \text{dose length product}^c},$$

with a, b and c being constant.

2. The computed tomography device according to claim 1, comprising a tube status device configured to determine a current tube status and whether the tube can perform the scan of the object based on the determined values of the scan parameters and the current tube status.

3. The computed tomography device according to claim 2, wherein the tube status device is a heat calculator device configured to determine whether the heat generated during the scan of the object using the determined values of the scan parameters is acceptable for the tube based on the current tube status and the determined values of the scan parameters.

4. The computed tomography device according to claim 1, wherein the at least one processor is configured to iteratively adapt one or more values of the scan parameters until an end condition occurs.

5. The computed tomography device according to claim 1, wherein the scan parameters include at least one of collimation aperture, rotation time, and pitch.

6. The computed tomography device according to claim 1, wherein the at least one processor is configured to determine the values of the scan parameters based on a look up table that comprises values of the scan parameters based on exposure time or determine the values of the scan parameters based on scan parameter functions that provide values for the scan parameters in dependence of exposure time.

7. The computed tomography device according to claim 1, wherein the at least one processor is configured to determine the z-dependent object size of the object along the z-axis based on a two-dimensional X-ray projection image of the object.

8. The computed tomography device according to claim 1, wherein the at least one processor is configured to generate a time dependent tube current profile based on the object specific exposure time, the z-dependent tube current by exposure time product, and the determined values of the scan parameters and to determine a time dependent power profile based on the time dependent tube current profile and the tube voltage used for the scan of the object.

9. A spiral computed tomography system, comprising:
a computed tomography device according to claim 1;
a tube for emitting X-rays;
a table configured to translate an object along a z-axis through the spiral computed tomography system; and
a detector for receiving the X-rays, wherein the table is arranged between the tube and the detector such that the X-rays emitted from the tube penetrate the object on the table and the X-rays are received by the detector.

10. A method for optimizing values of scan parameters for a scan of an object, comprising:
determining an object specific exposure time based on a maximal required value of a z-dependent tube current by exposure time product profile along a z-axis of an object and a maximal available tube current value of a tube used for a scan of the object, wherein the maximal available tube current value depends on a tube voltage and maximal electric power of the tube at given focal spot area, and wherein the z-dependent tube current by exposure time product profile is based on a dose index value or a pixel noise index value for the scan of the object, the tube voltage, and a z-dependent object size along the z-axis, and in which values of scan parameters for the scan of the object are determined based on the object specific exposure time; and
determining the values of the scan parameters based on maximizing a Figure of Merit that is defined as $$\text{Figure of Merit} = \frac{\text{table speed}^a}{\text{exposure time}^b \cdot \text{dose length product}^c},$$

with a, b and c being constant.

11. The method according to claim 10, further comprising:
providing the z-dependent object size of the object along the z-axis, the dose index value or the pixel noise index value for the scan of the object, the maximal electric power of the tube at the given focal spot area, and the tube voltage applied to the tube for the scan of the object;
calculating the maximal available tube current value of the tube based on the tube voltage and the maximal electric power of the tube at the given focal spot area;
calculating the z-dependent tube current by exposure time product profile along the z-axis based on the dose index value or the pixel noise index value, the tube voltage and the z-dependent object size along the z-axis;
extracting the maximal required value of the z-dependent tube current by exposure time product profile along the z-axis;
calculating the object specific exposure time based on the maximal required value of the z-dependent tube current by exposure time product along the z-axis and the maximal available tube current value;
determining the values of the scan parameters for the scan of the object based on the object specific exposure time;
generating a time dependent tube current profile based on the object specific exposure time, the z-dependent tube current by exposure time product along the z-axis, and the determined values of the scan parameters; and
generating a time dependent tube power profile based on the time dependent tube current profile and the tube voltage applied to the tube for the scan of the object.

12. The method according to claim 11, further comprising:
determining a current tube status of the tube; and
determining whether the tube can perform the scan of the object based on the time dependent tube power profile and the current tube status.

13. A non-transitory computer-readable medium having executable instructions stored thereon which, when executed by at least one processor, cause the at least one processor to perform a method for optimizing values of scan parameters for a scan of an object, the method comprising:
determining an object specific exposure time based on a maximal required value of a z-dependent tube current by exposure time product profile along a z-axis of an object and a maximal available tube current value of a tube used for a scan of the object, wherein the maximal available tube current value depends on a tube voltage and maximal electric power of the tube at given focal spot area, and wherein the z-dependent tube current by exposure time product profile is based on a dose index value or a pixel noise index value for the scan of the object, the tube voltage, and a z-dependent object size along the z-axis, and in which values of scan parameters for the scan of the object are determined based on the object specific exposure time; and
determining the values of the scan parameters based on maximizing a Figure of Merit that is defined as $$\text{Figure of Merit} = \frac{\text{table speed}^a}{\text{exposure time}^b \cdot \text{dose length product}^c},$$

with a, b and c being constant.

* * * * *